United States Patent [19]

Singh

[11] 4,347,363

[45] Aug. 31, 1982

[54] PROCESS FOR PREPARING 1,2-DIHYDRO-6-METHYL-2-OXO-5-(PYRIDINYL)NICOTINONITRILES

[75] Inventor: Baldev Singh, East Greenbush, N.Y.

[73] Assignee: Sterling Drug Inc., New York, N.Y.

[21] Appl. No.: 303,178

[22] Filed: Sep. 17, 1981

[51] Int. Cl.³ .......................................... C07D 213/85
[52] U.S. Cl. ..................................... 546/249; 546/250
[58] Field of Search ........................ 546/249, 250, 257

[56] References Cited

U.S. PATENT DOCUMENTS 4,223,149  9/1980  Opalka, Jr. et al. ................ 546/257
4,276,293  6/1981  Lesher et al. ........................ 546/118

Primary Examiner—Norma S. Milestone
Attorney, Agent, or Firm—Robert K. Bair; B. Woodrow Wyatt; Paul E. Dupont

[57] ABSTRACT

A process for preparing cardiotonically active 1,2-dihydro-6-methyl-2-oxo-5-(pyridinyl)nicotinonitriles which comprises reacting a pyridinylmethyl methyl ketone with ethoxymethylenemalononitrile, where pyridinyl is 4- or 3-pyridinyl or 4- or 3-pyridinyl having one or two lower-alkyl substituents.

3 Claims, No Drawings

PROCESS FOR PREPARING 1,2-DIHYDRO-6-METHYL-2-OXO-5-(PYRIDINYL)-NICOTINONITRILES

BACKGROUND OF THE INVENTION (a) Field of the Invention

This invention relates to a process for preparing cardiotonically active 1,2-dihydro-6-methyl-2-oxo-5-(pyridinyl)nicotinonitriles.

(b) Description of the Prior Art

Lesher, Opalka and Page U.S. Pat. No. 4,276,293, issued June 30, 1981 and based on application Ser. No. 135,211, filed Mar. 28, 1980, discloses the process for preparing a 1,2-dihydro-6-(lower-alkyl)-2-oxo-5-(pyridinyl)nicotinonitrile by first reacting a pyridinylmethyl lower-alkyl ketone with dimethylformamide di-(lower-alkyl) acetal to produce a 1-(pyridinyl)-2-(dimethylamino)ethenyl lower-alkyl ketone and then reacting said ketone with alpha-cyanoacetamide.

Opalka and Lesher U.S. Pat. No. 4,223,149, issued September 16, 1980, discloses and claims the process for preparing a 1,2-dihydro-2-oxo-5-(pyridinyl)nicotinonitrile by reacting alpha-(pyridinyl)-beta-[di-(lower-alkyl)amino]acrolein with malononitrile in a lower-alkanol.

SUMMARY OF THE INVENTION

The present invention resides in the process for preparing 1,2-dihydro-6-methyl-2-oxo-5-(pyridinyl)-nicotinonitriles by reacting a pyridinylmethyl methyl ketone with ethoxymethylenemalononitrile.

DETAILED DESCRIPTION INCLUSIVE OF PREFERRED EMBODIMENTS

The invention resides in the process which comprises reacting pyridinylmethyl methyl ketone with ethoxymethylenemalononitrile in a lower-alkanol to produce 1,2-dihydro-6-methyl-2-oxo-5-(pyridinyl)nicotinonitrile, where pyridinyl is 4- or 3-pyridinyl or 4- or 3-pyridinyl having one or two lower-alkyl substituents. In a preferred embodiment 4(or 3)-pyridinylmethyl methyl ketone and ethoxymethylenemalononitrile are heated in ethanol to produce 1,2-dihydro-6-methyl-2-oxo-5-[4(or 3)-pyridinyl]nicotinonitrile. In a particularly preferred embodiment 4-pyridinylmethyl methyl ketone and ethoxymethylenemalononitrile are heated in refluxing ethanol to produce 1,2-dihydro-6-methyl-2-oxo-5-(4-pyridinyl)nicotinonitrile.

The term "lower-alkyl" as used herein, e.g., as a substituent for "pyridinyl", means alkyl radicals having from one to four carbon atoms which can be arranged as straight or branched chains, illustrated by methyl, ethyl, n-propyl, isopropyl, n-butyl, 2-butyl or isobutyl.

The term "lower-alkanol" as used herein means an alkanol having from one to four carbon atoms, illustrated by methanol, ethanol, n-propanol, isopropyl alcohol, n-butanol, and the like.

The term "pyridinyl" as used herein, e.g., in the intermediate pyridinylmethyl methyl ketone and as the 5-substituent of the nicotinonitrile product of the process of the invention, means 4- or 3-pyridinyl or 4- or 3-pyridinyl having one or two "lower-alkyl" substituents, illustrated by 2-methyl-4-pyridinyl, 3-methyl-4-pyridinyl, 2-methyl-3-pyridinyl, 2,6-dimethyl-4-pyridinyl, 6-methyl-3-pyridinyl (alternatively named 2-methyl-5-pyridinyl), 2,3-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diisopropyl-4-pyridinyl, and the like.

The molecular structures of the products produced by the process of the invention were assigned on the basis of evidence provided by infrared, nuclear magnetic resonance and mass spectra, by chromatographic mobilities, and by the correspondence of calculated and found values for the elementary analyses for representative examples.

The manner of making and using the instant invention will now be generally described so as to enable a person skilled in the art of chemistry to make and use the same, as follows:

The process of the invention is carried out by heating the reactants, that is, a pyridinylmethyl methyl ketone and ethoxymethylenemalononitrile, in a lower-alkanol at about 60° C. to 120° C., preferably about 75° to 100° C., particularly preferably in refluxing ethanol.

The following examples will further illustrate the invention without, however, limiting it thereto.

EXAMPLE 1

A mixture containing 13.5 g. of 4-pyridinylmethyl methyl ketone, 12.2 g. of ethoxymethylenemalononitrile and 100 ml. of ethanol was refluxed with stirring for five hours and then allowed to cool to room temperature. The separated crystalline product was collected, washed with cold ethanol and dried in a vacuum oven at 60° C. to yield 14.2 g. of 1,2-dihydro-6-methyl-2-oxo-5-(4-pyridinyl)nicotinonitrile, m.p. >300° C. The nuclear magnetic resonance and infrared spectra of this product were identical with the corresponding respective spectra of the same compound prepared by a different method, that is, by reacting 1-(4-pyridinyl)-2-(dimethylamino)ethenyl methyl ketone with alpha-cyanoacetamide. Also, a mixed melting point with the same compound prepared by said different method showed no depression.

Following the procedure described in Example 1 but using in place of 4-pyridinylmethyl methyl ketone a molar equivalent quantity of the appropriate pyridinylmethyl ketone, it is contemplated that there can be obtained the corresponding 1,2-dihydro-6-methyl-2-oxo-5-(pyridinyl)nicotinonitriles of Examples 2 through 5.

2. 1,2-Dihydro-6-methyl-2-oxo-5-(3-pyridinyl)-nicotinonitrile, using 3-pyridinylmethyl methyl ketone.

3. 1,2-Dihydro-6-methyl-5-(2-methyl-4-pyridinyl)-2-oxonicotinonitrile, using (2-methyl-4-pyridinyl)methyl methyl ketone.

4. 5-(2-Ethyl-4-pyridinyl)-1,2-dihydro-6-methyl-2-oxonicotinonitrile, using (2-ethyl-4-pyridinyl)methyl methyl ketone.

5. 1,2-Dihydro-6-methyl-5-(2,6-dimethyl-4-pyridinyl)-2-oxonicotinonitrile, using (2,6-dimethyl-4-pyridinyl)methyl methyl ketone.

I claim:

1. The process which comprises reacting pyridinylmethyl methyl ketone with ethoxymethylenemalononitrile in a lower-alkanol to produce 1,2-dihydro-6-methyl-2-oxo-5-(pyridinyl)nicotinonitrile, where pyridinyl is 4- or 3-pyridinyl or 4- or 3-pyridinyl having one or two lower-alkyl substituents.

2. The process according to claim 1 where 4(or 3)pyridinylmethyl methyl ketone and ethoxymethylenemalononitrile are heated in ethanol to produce 1,2-dihydro-6-methyl-2-oxo-5-[4(or 3)-pyridinyl]-nicotinonitrile.

3. The process according to claim 1 where 4-pyridinylmethyl methyl ketone and ethoxymethylenemalononitrile are refluxed in ethanol to produce 1,2-dihydro-6-methyl-2-oxo-5-(4-pyridinyl)nicotinonitrile.

* * * * *